(12) United States Patent
Iijima

(10) Patent No.: US 6,365,384 B1
(45) Date of Patent: Apr. 2, 2002

(54) METHOD FOR DISPOSING WASTE

(76) Inventor: Ryusuke Iijima, 1-3-7 Koyamadai, Sakae-Ku, Yokohama city, Kanagawa, 247-0002 (JP)

( * ) Notice: Subject to any disclaimer, the term of this patent is extended or adjusted under 35 U.S.C. 154(b) by 0 days.

(21) Appl. No.: 09/524,923

(22) Filed: Mar. 14, 2000

Related U.S. Application Data

(63) Continuation-in-part of application No. 09/305,838, filed on May 5, 1999, now abandoned.

(51) Int. Cl.$^7$ ......................... C12N 11/00; C12N 11/02; C12N 11/14; C12N 1/20
(52) U.S. Cl. ................. 435/174; 210/600; 210/602; 210/610; 435/176; 435/177; 435/252.1; 435/254.1; 435/262.5
(58) Field of Search ................................ 210/600, 602, 210/610; 435/262.5, 254.1, 174, 176, 177, 252.1

(56) References Cited

U.S. PATENT DOCUMENTS 5,580,458 A * 12/1996 Yamasaki et al. ............ 210/609
5,756,304 A *  5/1998 Jovanovich ................... 435/34

\* cited by examiner

*Primary Examiner*—David M. Naff
*Assistant Examiner*—Deborah K Ware
(74) *Attorney, Agent, or Firm*—Curtis L. Harrington

(57) ABSTRACT

A method for disposing waste such as agricultural waste, sludge, livestock excreta, food and residue, is disclosed. The method includes the steps of a mycelial carrier-support comprising 80–95% by weight of a porous carrier of 3–30 mesh in particle size in the state of pH of 6.5–9.5. The carrier can be charcoal, active carbon, coal, coke, active coke, peat, palmculite, and bentonite. Furthermore, a thermophile is used as the main bacterial ingredient, such as *Bacillus subtilis*. Fungi are also part of the carrier-support. The fungi include Thermoactinomyces, Thermonospora, Actinbifida and Thermopolyspora.

4 Claims, No Drawings

METHOD FOR DISPOSING WASTE

This application is a continuation-in-part of application Ser. No. 09/305,838 filed May 5, 1999, now abandoned.

TECHNICAL FIELD

The present invention relates to a method for disposing waste, and the object thereof is to provide a waste disposal method wherein the organic waste including sludge from both water supply and sewerage, livestock excreta such as fowl droppings and pig excrement, carcasses of livestock, agricultural waste such as dried grass and rotten crops, and raw garbage such as both animal-based and vegetable-based food residue is fermented and decomposed efficiently in a short time of period, and is disposed and then recycled so that the waste can be used effectively.

BACKGROUND ART

Presently, the industrial waste such as sludge, excreta and constructive wooden waste is discharged about four hundred million tons per year in our country. Within these industrial waste, about one hundred and fifty million tons are recycled, yet the rest (i.e. two hundred and fifty million tons of the industrial waste) and most of the ordinary waste are disposed by incineration and landfill.

However in these days, incineration disposal and landfill disposal are getting difficult as the amount of the waste is increasing. The ways of collecting waste and recycling them are argued.

For instance, although the organic waste such as the sludge from both water supply and sewerage, livestock excreta such as fowl droppings and pig excrements, carcasses of livestock, agricultural waste like dried grass and rotten crops, and raw garbage such as both animal-based and vegetable-based food residue can be recycled, most of the above are incinerated. Recently, these organic waste are on trial to be used as compost by fermented accumulation.

Also, due to the prohibition in the usage of mixed agricultural chemicals such as poisonous DDT and BHC and chemical fertilizers, using non-poisonous agricultural waste and animal-based and vegetable-based food residue effectively as compost is getting more necessary in the U.S.A. recently.

PROBLEMS TO BE SOLVED BY THE INVENTION

However, it takes about 1 to 6 months to ferment the waste if the organic waste are disposed as compost by fermented accumulation. Therefore, the usage of waste as compost is not efficient. Moreover, since the organic waste with some water contained such as sludge and both animal-based and vegetable-based food residue are easily decayed and changeable in their states, the surrounding environment can be affected by their bad smell. It is more likely that the efficiency of recycling waste is not very high. A method of disposing waste wherein sludge from both sewerage and water supply, livestock excreta like fowl droppings and pig excrement, carcasses of livestock, agricultural waste like dried grass and rotten crops, and raw garbage including both animal-based and vegetable-based food residue are fermented and decomposed efficiently in a short period of time, and are disposed and then recycled so that the waste can be used effectively, has been sought.

SUMMARY OF THE INVENTION

The present invention is to solve the said problems. The invention as set forth in claim 1 comprises the steps of:

a mycelial carrier-support comprising 80–95% by weight of a porous carrier of 3–30 mesh in particle size in the state of pH 6.5–9.5 comprising at least one kind selected from charcoal, active carbon, coal, coke, active coke, peat, palmculite, perlite, and bentonate;

providing from 5–20% by weight of bacterium and fungi mixture in which *Bacillus subtilis* of a thermophile is present as a majority of bacterium present, and more than one kind of a genus selected from a list consisting of Thermoactinomyces genus, Thermonospora genus, Actinbifida genus and Thermopolyspora genus;

a waste into which 5–40% by weight of this mycelial carrier-support to a weight of waste are added are fermented by agitating in an atmosphere where a fermentation system temperature is maintained at more than 15° C.;

as the fermentation temperature, which is maintained at 55–80° C. by aeration, starts to rise, the waste is decomposed. The invention as set forth in claim 2 relates to a method for disposing waste as set forth in claim 1 comprising that said waste is an organic waste which comprises more than one kind of waste selected from agricultural waste, food residue, sludge, human waste and wooden waste. The invention as set forth in claim 3 relates to a method for disposing waste as set forth in claim 1 wherein said mycelial carrier-support waste mixture after decomposition is admixed with soil to enrich said soil.

DETAILED DESCRIPTION OF THE PREFERRED EMBODIMENT

In the present invention, the waste can be disposed of by adding mycelial carrier-support.

The examples of the organic waste are the sludge isolated from water supply and sewerage at water treatment plants like water purifying plant, sewage treatment plant, human waste treatment plant and industrial effluent treatment plant; animal-based food residue such as meat and fish; vegetable-based food residue such as vegetable, seaweed and leftover rice; raw garbage like okara, extracted coffee residue and extracted sugarcane residue; extracted seaweed residue; livestock excreta like fowl droppings and pig excrements; carcasses of livestock; agricultural waste like dried grass and rotten crops; and human waste. It also includes wooden waste such as paper sludge, wood flour and wood bark.

If water contained 70–100% by weight of such waste, it is better to dehydrate down to 50–60%, so that the waste can be fermented efficiently. Moreover, it is much better to fracture the waste in order to maintain the temperature for aeration that will be mentioned later.

The mycelial carrier-support used in the present invention comprises 80–95% by weight of a porous carrier and has 5–20% by weight of mycelium. It can be obtained through the method which has been disclosed by the present inventor in both Japanese patent publication No. 5-59079 and U.S. Pat. No. 5196042.

The mycelium supported by the porous carrier is an association of thermoactinomycetes and microorganisms leading thermophile. Using such thermoactinomycetes and the mycelial carrier-support which supports the mycelium predominated by the thermophile, the waste can be fermented and decomposed efficiently.

The thermoactinomycetes is an actinomycetes which can grow at the temperature of 55–80° C. In this invention, the actinomycetes that belongs to at least one genus selected from Thermoactinomycetes genus such as *Thermoactinomyces vulgaris,* Thermomonospora genus such as *Ther-*

*momonospora chromogena*, Actinobifida genus such as *Actinobifida dichotomia*, and Thermopolyspora genus such as *Thermopolyspora flexuosa*.

Also, the thermophile is bacterium which can grow at the temperature of 55–80° C. In this invention, *Bacillus subtilis* is used.

The porous carriers which support the mycelium comprise at least one kind selected from carbonated porous carrier such as charcoal, active carbon, coal, coke, active coke, peat and palmculite; perlite and bentonate. It is possible to use the porous carriers which comprise more than two kinds selected from the above.

The mycelial carrier-support comprising such porous carriers can hold enough water and air which are the necessary components for the growth of the thermoactinomycetes and the thermophile, and does not disturb the growth of the thermoactinomycetes and the thermophile while adding them into the waste, and it perfectly ferments the waste.

The pH of the porous carrier is pH 6.5–9.5 which is the appropriate pH range for the growth of the thermoactinomycetes and the thermophile. Therefore, it prevents the growth of harmful fungi such as germs and filamentaous fungi which hardly grow under the condition of alkaline, and the fermentation with the thermoactinomycetes and the thermophile can be done efficiently.

Also the particle size of the porous carrier is limited to 3–30 mesh. Therefore, in the fermenting stage with the mycelium, the fermentation temperature can be maintained at 55° C. above, and the waste can be composed completely with the themoactinomycetes and the thermophile.

By adding such mycelial carrier-support into said organic waste, the waste is fermented, decomposed and disposed.

The amount of the mycelial carrier-support added has to be 5–40% by weight of this mycelial carrier-support to a weight of waste. In case of the amount of the mycelial carrier-support added is reduced, the waste cannot be decomposed favorably, and in case the amount of the mycelial carrier-support added is increased, the favorable fermentation temperature cannot be obtained because the water supplied from the waste as the water content of the fermented substances reduces. Neither of the above mentioned cases is favorable.

The fermentation conditions for fermenting the waste by adding the mycelial carrier-support are explained hereinafter.

Firstly, the waste is fermented under the favorable condition while agitating the mycelial carrier-support added waste in an atmosphere where a temperature of the fermentation system is maintained at more than 15° C. This is to keep the uniformity of fermentation by keeping the constant temperature with the system temperature from the outside temperature. The reason for the system temperature to be above 15° C. is that the fermentation temperature does not sufficiently rise favorably in the case of the temperature is below 15° C. Then, as the fermentation temperature which is maintained at 55–80° C. by aeration starts to rise, the waste is fermented and it can be completely decomposed and disposed in a short time of period with the work of said thermoactinomycetes and said thermophile.

The method for disposing waste which relates to the present invention is explained above, and according to this method, the waste can be completely decomposed and disposed of in a short time of period. In other words, in case of using the customary fermented accumulation method, it takes 1–6 month(s) to ferment the waste completely, but the method related to this invention, the waste can be disposed of within 7–14 days. Therefore, the waste can be efficiently disposed and effectively recycled. Moreover, since the obtained compost has effects in promoting the growth of plants and in preventing the obstacles of continuous cropping, it can be used as a plant activator and as a soil regulator.

The smell of the waste can be reduced down to $½–1/100$, thus reduces odor. Furthermore, the volume of the waste can be reduced to $1/10$, thus the volume can be reduced.

EMBODIMENTS

The following are the detailed explanations of the present invention that are based on both embodiments and comparative examples. It needs to noted that the present invention is not limited within the embodiments.

(Embodiment 1)

25.5 Kg of coconut-husk charcoal of pH 8.2, 25 mesh pass in particle size and 200 $m^2/g$ of the internal surface area and 4.5 kg of mycelium comprising *Thermoactinomyces vulgaris, Thermomonospora chromogena, Actinobifida dichotomia, Thermopolyspora flexuosa* and *Bacillus subtilis* were supported to prepared as the mycelium carrier-support.

30 Kg (50 l) of such mycelial carrier-support was added and kneaded into 500 l of waste comprising bird carcasses and their internal organs which contained 60–80% of water. This mixture was then fermented by agitating within the fermentor wherein the temperature was maintained at 25° C. As the fermentation temperature started to rise, it was maintained at about 70° C. by aeration, and the waste was fermented further. As a result, the water content of the waste became under 30%, and the waste was completely decomposed with no bad smell after seven days.

COMPARATIVE EXAMPLE 1

The same 500 l of waste used in said Embodiment 1 was put into the fermentor, and then was fermented using the same method as Embodiment 1 except for the addition of the mycelial carrier-support. After seven days of fermentation, the waste was taken out. Most of the waste was not decomposed, and the situation was almost in the same condition as the the waste which had been put into the fermentor. Then, the waste was fermented until it was completely decomposed. This took about one and half month.

(Embodiment 2)

30 Kg (50 l) of such mycelial carrier-support which was used in Embodiment 1 was added and kneaded into 500 l of waste comprising fowl droppings and pig excrements which contained 70–80% of water. This mixture was then fermented by agitating within the fermentor wherein the temperature was maintained at 25° C. As the fermentation temperature started to rise, it was maintained at about 60° C. by aeration, and the waste was fermented further. As a result, the water content of the waste became under 30%, and the waste was completely decomposed with no bad smell after seven days.

COMPARATIVE EXAMPLE 2

The same 500 l of waste used in said Embodiment 2 was put into the fermentor, and then was fermented using the same method as Embodiment 2 except for the addition of the mycelial carrier-support. After seven days of fermentation, the waste was taken out. Most of the waste was not decomposed, and the situation of it was almost same as one of the waste which had been put into the fermentor. Then, the waste was fermented until it was completely decomposed. This took about two months.

(Embodiment 3)

1,000 Kg of waste having a water content between 70–90% and comprising residue made by which alginic acid was extracted from brown algae including tangles and wakame seaweeds and diatom earth was kneaded with 50 kg of mycelial carrier-support used in the embodiment 1. The waste was fermented while the kneaded mixture was agitated in a fermentor where the temperature was maintained at 25° C. Then, as the fermentation temperature started to rise, it was further fermented while the fermentation temperature was restored at about 80° C. by aeration. As a result, 14 days later, the water content of the waste became 32% and the waste was completely decomposed. Before the fermentation, the waste had emitted a terrible smell, but after the fermentation, the bad smell was completely gone.

COMPARATIVE EXAMPLE 3

1,000 Kg of waste the same as the above embodiment 3 was stored except for the addition of the mycelial carrier-support in a fermentor in which a temperature was maintained at 25° C. and fermented while the fermentation temperature was maintained at about 50° C. by aeration. After it had been fermented for 14 days, the waste was scarcely decomposed and the situation was almost in the same condition as the waste which had been put into the fermentor. Thereafter it had been fermented until it was completely decomposed. As a result, it took about two months that the waste was completely decomposed. A bad smell became about 42% less than before the fermentation, but still emitted the bad smell.

(Embodiment 4)

As a porous carrier, charcoal of 20 mesh in particle size in the state of pH 8.3 is used and *Thermoactinomyces vulgaris, Thermomonospora chromogena, Actinobifida dichotomica, Thermopolyspora flexuosa* and *Bacillus subtilis,* all of which had been cultivated in a culture medium of an yeast extraction of powdery maltose were supported so that a mycelial carrier-support was obtained.

Waste comprising sludge separated from sewerage-treatment plant and night soil treatment plant was dehydrated to have a water content between 50–60%, and 500 l of the waste was added and kneaded with 30 kg (50 l) of said mycelial carrier-support. The waste was fermented while the kneaded mixture was agitated in a fermentor in which the temperature was maintained at 25° C. As the fermentation temperature started to rise, it was further fermented while the fermentation temperature was restored at about 65° C. by aeration. As a result, 13 days later, the water content of the waste became less than 30% and the waste was completely decomposed. In addition, the waste did not emit bad smell.

COMPARATIVE EXAMPLE 4

500 l of waste the same as the waste in above embodiment 4 was put into a fermentor, and the waste was fermented the same as one of embodiment 4 except for the addition of a mycelial carrier-support material. After it had been fermented for 7 days, the waste was taken out from the fermentor. The waste was scarcely decomposed and the situation was almost in the same condition as when it was put into the fermentor. Therefore, it was further fermented until most of the waste was not decomposed. It took about two months that the waste was completely decomposed.

(Embodiment 5)

500 Kg of waste comprising animal-based and vegetable-based food residue was added and kneaded with 50 kg of the mycelial carrier-support used in embodiment 1. The waste was fermented while the kneaded mixture was agitated in a fermentor where a temperature was maintained at 25° C. As the fermentation temperature started to rise, it was further fermented while the fermentation temperature was restored at about 80° C. by aeration. As a result, 7 days later, the water content of the waste became less than 35% and the waste was completely decomposed.

COMPARATIVE EXAMPLE 5

500 Kg of waste the same as one of said embodiment 5 was put into a fermentor and fermented the same as embodiment 5 except for the addition of a mycelial carrier-support. After it was fermented for 7 days, the waste was taken out. Most of the waste was not decomposed and the condition of the waste was almost the same as when it was put into the fermentor. Thereafter, it was further fermented, and it took about two months that the waste was completely decomposed.

(Embodiment 6)

1000 Kg of waste comprising paper sludge and wood bark was added and kneaded with 50 kg of a mycelial carrier-support which was used in embodiment 1. The waste was fermented while the kneaded mixture was agitated in a fermentor where a temperature was maintained at 25° C. As a fermentation temperature started to rise, it was further fermented while the fermentation temperature was restored at about 65° C. by aeration. As a result, 30 days later, the water content of the waste became less than 30% and the waste was completely decomposed.

COMPARATIVE EXAMPLE 6

1000 Kg of waste the same as one of said embodiment 6 was put into a fermentor and fermented the same as embodiment 6 except for the addition of a mycelial carrier-support. After it had been fermented for 30 days, the waste was taken out. The most waste was not decomposed and the situation of the waste was almost the same as one put into the fermentor. Thereafter, it was further fermented, and it took about six months before the waste was completely decomposed.

As seen in results of above mentioned embodiments and comparative examples, by disposing waste by adding a mycelial carrier-support made by which porous carrier is retained in mycelium, livestock excreta like fowl droppings and pig excrements, carcasses of livestock, agricultural waste like dried grasses and rotten crops, food residue, sludge, human waste, wooden waste can be treated effectively in a short time of period such as 7–30 days.

Tests employing compost obtained by a method for disposing waste relating to the present invention were conducted as below.

Test Example 1

Compost obtained by which fowl droppings were treated by the method of embodiment 2 was used as a fertilizer for an embodiment A while compost obtained by sludge treated by the method of embodiment 4 was used as a fertilizer for an embodiment B.

In a flower center located in Kyoto prefecture, employing soil comprising that 20% of the fertilizers of embodiment A and B are mixed with pure soil, tests for growth of flower seeding of cloleus, sage and marigold were conducted. As control tests, tests for growth in control A wherein rotten leaves and pure soil were mixed in the proportion of 2 to 1 and control B wherein rotten leaves, pure soil and chaff are mixed in the proportion 5:3:2 were conducted.

One month later, each condition of growth of three seedings were respectively evaluated by 5 steps.

As a result in the table 1 shows, the fertilizer obtained by the method for disposing waste relating to the present invention is superior from the point of view of an effect of promoting the growth of plants.

Test Example 2

Using the fertilizer of the above embodiment A, a test for a prevention of a barrier of a repeated cultivation of mulukhiyya was conducted in a field located in Mito city in Ibaragi prefecture.

In a plastic greenhouse about 80 tsubo (about 264 m$^2$) where soil comprised soil+compost+fowl droppings+compound fertilizer, in the left side about 40 tsubo (132 m$^2$), 12.5 l of the fertilizer of embodiment A was scattered and was allowed to be a treatment while the right side was allowed to be a control. After plowing the whole field, mulukhiyya were repeatedly planted.

One month later, observing a condition of all leaves of an each mulukhiyya in each area, leaves of mulukhiyya planted in the treatment where the fertilizer of embodiment A was scattered were vividly green and grew well. On the other hand, it was apparent that leaves of mulukhiyya planted in the control grew slower compared with ones planted in the treatment. All leaves of five stumps of mulukhiyya in a respective area were cut and measured a weight of leaves per one stump of mulukhiyya. The result was shown in table 2.

As the result of the above test, it is apparent that the fertilizer obtained by the method for disposing waste relating to the present invention has an effect of a prevention of a barrier of a repeated cultivation as well as an effect of promoting a growth of plant.

Effect of the Invention

As described above, the present invention relating to claim 1 is a method for disposing waste comprising the steps of:

a mycelial carrier-support comprising 80–95% by weight of a porous carrier of 3–30 mesh in particle size in the state of pH 6.5–9.5 comprising at least one kind selected as charcoal, active carbon, coal, coke, active coke, peat, palmculite, perlite, bentonite;

providing from 5–20% by weight of bacterium and fungi mixture in which *Bacillus subtilis* of a thermophile is present as a majority of bacterium present, and more than one kind of a genus selected from a list consisting of Thermoactinomyces genus, Thermomonospora genus, Actinbifida genus and Thermopolyspora genus, a waste into which 5–40% by weight of this mycelial carrier-support to a weight of waste are added are fermented by agitating in an atmosphere where a fermentation system temperature is maintained at more than 15° C. and that as a fermentation temperature starts to rise, the fermentation temperature is restored between 55–80° C. by aeration so that the waste is decomposed. The present invention relating to claim 2 is a method for disposing waste as set forth in claim 1 comprising that said waste is a organic waste which comprises more than one kind of waste selected from agricultural waste, food residue, sludge, human waste and wooden waste. The present invention relating to claim 3 is a method for disposing waste as set forth in claim 1 wherein said mycelial carrier-support waste mixture after decomposition is admixed with soil to enrich said soil. Therefore, organic waste such as sludge from both sewerage and water supply, livestock excreta like fowl droppings and pig excrements, carcasses of livestock, agricultural waste like dried grasses and rotten crops, and raw garbage like both animal-based and vegetable-based food residue are fermented and decomposed effectively in a short time of period, and are disposed and then recycled so that the waste can be used effectively.

In addition, since the amount of the mycelial carrier-support material to be added is set in the proportion of 5–40% by a weight to a weight of waste, and waste is fermented by agitating the mixture in an atmosphere where a fermentation system temperature is maintained at more than 15° C., a favorable fermentation temperature is obtained, the uniformity of fermentation is maintained and the fermentation by thermoactinomycetes and thermophile can effectively occurr. Therefore, superior compost having high capabilities such as an effect of prompting growth of plant and a prevention of the obstacles of continuous cropping can be obtained by the present invention.

TABLE 1

|  | Coleus | Sage | Marigold |
| --- | --- | --- | --- |
| Embodiment A | 4 | 4 | 5 |
| Embodiment B | 5 | 5 | 5 |
| Control A | 1 | 0 | 2 |
| Control B | 2 | 1 | 2 |

TABLE 2

|  | A Weight of leaves per stump | | | | | Total |
| --- | --- | --- | --- | --- | --- | --- |
| Treatment | 64 g | 70 g | 58 g | 67 g | 61 g | 320 g |
| Control | 35 g | 30 g | 22 g | 39 g | 41 g | 167 g |

What is claimed is:

1. A mycelial carrier-support comprising:

80–95% by weight of a porous carrier of 3–30 mesh in particle size having a pH of from about 6.5 to about 9.5 selected from the group consisting of charcoal, active carbon, coal, coke, active coke, peat palmculite, perlite and bentonite; and 5–20% by weight of a mixture of bacteria and fungi in which *Bacillus subtilis* thermophile is present as a majority of said bacteria and wherein said fungi comprises a fungi of the genus selected from the group consisting of Thermoactinoymyces, Thermospora, Actinbifida and Thermopolyspora.

2. A method for disposing of waste comprising the steps of:

provviding a mycelial carrier-support comprising 5–20% of a mixture of fungi and bacteria and 80–95% by weight of a porous carrier of 3–30 mesh in particle size having a pH of from about 6.5 to 9.5 selected from the group consisting of charcoal, active carbon, coal, coke, active coke, peat, palmculite, perlite and bentonite wherein said mixture of fungi and bacteria comprises a fungi of the genus selected from the group consisting of Thermoactinomyces, Thermonospora, Actinbifida and Thermopolyspora and a *Bacillus subtilis* thermophile as a majority of said bacteria;

adding 5–40% by weight of said mycelial carrier-support to waste to be decomposed and fermenting the waste by agitating at a temperature of more than 15 degrees Celsius; and allowing said temperature to rise and continue fermenting said waste at a temperature maintained between 55–80 degrees Celsius by aeration so that the waste is decomposed.

3. The method for disposing waste as set forth in claim 2 wherein said waste is an organic waste selected from the group consisting of agricultural waste, food residue, sludge, human waste and wooden waste.

4. The method for disposing waste as set forth in claim 2 wherein a mixture of said decomposed waste and said mycelial carrier-support is obtained, and said mixture is admixed with a soil to enrich said soil.

* * * * *